United States Patent
Wyss et al.

(10) Patent No.: US 6,913,746 B2
(45) Date of Patent: Jul. 5, 2005

(54) COMPLEXES OF IMMUNOGLOBULINS POLYSACCHARIDES FOR ORAL AND TRANSMUCOSAL ABSORPTION

(75) Inventors: Rolando Wyss, Vaduz (LI); Bernad Bizzini, Albi (FR); Ivo Volpato, San Mariano (IT)

(73) Assignee: Grisotech S.A., Soazza (CH)

( * ) Notice: Subject to any disclaimer, the term of this patent is extended or adjusted under 35 U.S.C. 154(b) by 142 days.

(21) Appl. No.: 10/081,081

(22) Filed: Feb. 20, 2002

(65) Prior Publication Data

US 2003/0068315 A1 Apr. 10, 2003

(30) Foreign Application Priority Data

Feb. 21, 2001 (IT) ..................... MI2001A0347

(51) Int. Cl.⁷ ..................... A61K 39/395; A61K 39/40; A61K 39/42
(52) U.S. Cl. ............... 424/130.1; 424/137.1; 424/145.1; 424/146.1; 424/147.1; 424/152.1; 424/158.1; 424/159.1; 424/164.1
(58) Field of Search ................ 424/130.1, 137.1, 424/145.1, 146.1, 147.1, 152.1, 158.1, 159.1, 164.1

(56) References Cited

U.S. PATENT DOCUMENTS

| | | | |
|---|---|---|---|
| 5,380,513 A | | 1/1995 | Gray et al. |
| 5,429,952 A | * | 7/1995 | Garner et al. |
| 5,530,102 A | | 6/1996 | Gristina et al. |
| 5,679,639 A | * | 10/1997 | Griffin et al. |
| 5,747,475 A | | 5/1998 | Nordquist et al. |
| 6,036,978 A | * | 3/2000 | Gombotz et al. |
| 2003/0149254 A1 | * | 8/2003 | Anderson et al. |

FOREIGN PATENT DOCUMENTS

| | | |
|---|---|---|
| EP | 0315456 | 5/1989 |
| WO | WO9609805 | 4/1996 |
| WO | WO9730148 | 8/1997 |
| WO | WO9749732 | 12/1997 |
| WO | WO9837200 | 8/1998 |
| WO | WO9934831 | 7/1999 |
| WO | WO9830207 | 11/1999 |

OTHER PUBLICATIONS

Costa et al (ATAS Soc Biol Rio De J vol. 26 pp 15–24), 1986.*

* cited by examiner

Primary Examiner—Mark Navarro
(74) Attorney, Agent, or Firm—Abelman, Frayne & Schwab

(57) ABSTRACT

The present invention relates to complexes consisting of immunoglobulins and polysaccharides for oral and transmucosal use.

The polysaccharides comprised in the complexes according to the invention form an envelope which protects and carries immunoglobulins allowing their systemic absorption through the gastric and mucosal district. Immunoglobulins have a different specificity depending on the required therapeutic effect. They are used in passive immunoprophylaxis for the prevention or therapy of infections caused by pathogenic agents such as virus, bacteria, parasites, or they are used in the modulation of endogenous bio-chemical balances, or in the detoxification from drugs of abuse, medicines, toxins.

17 Claims, No Drawings

COMPLEXES OF IMMUNOGLOBULINS POLYSACCHARIDES FOR ORAL AND TRANSMUCOSAL ABSORPTION

FIELD OF THE INVENTION

The technical field of the present invention is immunotherapy.

STATE OF THE ART

The use of immunoglobulins in the clinical field is now limited to the possibility of parenteral administration. Immunoglobulins in parenteral administration are used to give passive immunization after exposure to pathogenic agents, or in cases of detoxification after consumption of drugs of abuse (cocaine), intoxication caused by natural toxins, or in cases of overdose of medicines.

Parenteral administration requires the intervention of medical and/or skilled personnel.

The use of immunoglobulins through oral or transmucosal administration, the latter making consumption easier, is a quite difficult objective to be reached because of the presence in gastric and mucosal areas of proteolytic enzymes and an acidic environment which would inactivate said protein macromolecules.

As a matter of fact, oral and transmucosal absorption requires that immunoglobulins are protected and carried until their complete absorption in the bloodstream. At the state of the art there are several studies aiming at enabling the passage through the mucosae of macromolecules of proteic and/or peptidic nature. For example, it has been observed that the incorporation into chitosane (in particular cross-linked chitosane) of antigenic structures and vaccines (e.g. gD2 protein of Herpex Simplex virus, described in Ugozzoli et al. *Immunology* 1998, 93(4):563–71; hemoagglutinine and *Bordertella pertussis* toxin, described in Jabbal-Gill et al., *Vaccine* 1998, 16(20):2039–46) or of peptides or hormones having preferably a medium-low molecular weight (such as insulin and hGH, described in EP 0952822), can allow transmucosal absorption.

In these cases chitosane is generally cross-linked and produced in microspheres having suitable size.

In WO 96/09805 is described the preparation of complexes comprising chitosan and antigens. In this case chitosan has the function to potentiate the immune response.

WO 99/34831 describes the coupling of therapeutic or diagnostic agents with carriers able to disrupt the endosomal membrane, favouring the transport inside the cell. In WO 97/30148 are disclosed the anti-allergenic properties of polipetides conjugated with different polymeric carrier molecules. In WO 98/37200 is described the preparation of conjugates between anti-IL-8 antibody and polymeric supports. In U.S. Pat. No. 5,747,475 is described the preparation of chitosan derived biomaterials as immunoadjuvants and for use in laser assisted tumor therapy.

In EP 315456 dextran is covalently linked to immunoglobulins to reduce their antigenicity in immunotherapy. U.S. Pat. No. 5,530,102 describes biodegradable supports for immunoglobulin used for in situ protection at a wound site.

SUMMARY

The main object of the present invention are complexes of immunoglobulins and polysaccharides for pharmaceutical use. In the complexes according to the invention polysaccharides are chosen among: chitosane, chitosane having a low molecular weight and a high degree of deacetylation, methylglycolchitosane, alginic acid, polymanuronic acid and their salts or derivatives. In the complexes according to the invention immunoglobulins and polysaccharides are associated by means of non-covalent links, preferably ionic links.

The immunoglobulins of the complexes according to the invention are chosen among IgG, IgA, or their fragments F(ab')2 or F(ab). Immunoglobulins are specific for exogenous agents such as external pathogenic agents, virus, bacteria, parasites or their antigenic fragments, or for toxins of mycotic origin, drugs, medicines; they can also be specific for endogenous bioactive substances, consisting of hormones, enzymes and proenzymes, bioactive peptides, metabolites, physiological precursors. They can be useful if it is necessary to modify endogenous levels of said substances both in pathologic situations and in normofunctional situations. Immunoglobulins having different specificities can also be associated in one complex to obtain a unique or synergic therapeutic effect.

The present invention considers as particularly preferred those complexes in which immunoglobulins are specific for: toxins of mycotic origin, or for medicines such as: monensin, corticosteroids, antibiotics, etc., or for virus, or for bacteria such as: *Listeria monocytogenes, Salmonella thipy, s. entheriditis* or for their antigenic components, which are typical cases of passive immunoprophylaxis. Complexes are also preferred, in which immunoglobulins are specific for hormones such as: chorionic gonadotropin, parathormone, glucagon, or for endogenous proenzyme prothrombin, and also for drugs of abuse such as: cocaine, heroine, lysergic acid and their salts and derivatives.

In such complexes the polysaccharides form a protective envelope around immunoglobulins and thus enable the oral and transmucosal absorption of the latter and their use beyond parenteral administration only.

Another object of the present invention is the use of said complexes of polysaccharides and immunoglobulins in the preparation of detoxifying medicines, of medicines for curing syndromes caused by drug overdose, of anti-ulcer medicines, of medicines for curing growth problems.

A further object of the present invention are pharmaceutical compositions containing as active agent the complexes according to the invention, associated or not with suitable excipients and adjuvants, among which the preferred one is the delipidated fraction of *C. granulosum*.

DETAILED DESCRIPTION OF THE INVENTION

The object of the present invention is represented by complexes of immunoglobulins (Ig) incorporated into polysaccharidic polymers wherein the polysaccharide is not chemically cross-linked to immunoglobulins and allows the systemic delivery of immunoglobulins. Immunoglobulins are in the form of fragments F(ab) with a molecular weight of about 50 kD, or of fragments F(ab')$_2$ with a molecular weight of about 100 kD, or in the 150 kD form (Ig).

The authors have found that—and this represents the main object of the present invention—absorption through the enteral (oral) and/or transmucosal way allowing a systemic delivery of protein macromolecules, is efficiently achieved by coating such macromolecules with polysaccharides preferably derivatives of chitosane and/or alginic acid, with no limitations on molecular weight of the polysaccharide chosen.

The possibility to make immunoglobulins bioavailable (absorbable) by the oral and transmucosal way (perlingual, nasal, vaginal, rectal) opens up a series of new applications for the pharmaceutical use of these macromolecules.

Oral or transmucosal absorption is above all easier than parenteral administration: as a matter of fact, such kind of administration does not require the intervention of medical and/or skilled personnel.

According to a first embodiment the present invention is represented by complexes comprising immunoglobulins incorporated into polysaccharides, wherein the polysaccharides externally coat the immunoglobulins, carrying the latter, protecting their proteic structure and allowing a systemic delivery in an active form through the oral and transmucosal way. In the complexes of the invention polysaccharides and immunoglobulins are not linked through covalent links, but are rather associated through nonspecific interactions, such as van der Waals forces or ionic interactions.

The oral (enteral) or/and transmucosal administration presents a series of advantages with respect to parenteral administration even though providing a systemic way of action. In the present case of immunoglobulins, the enteral and transmucosal administration allows a slower and more gradual absorption of Ig and allows to control to a higher extent the dosage and the distribution in the bloodstream of said proteins without altering their efficacy. On the contrary, expecially in the case of repeated treatments with heterologous proteins, parenteral administration determines a fast increase in the level of heterologous macromolecules in the bloodstream which can result in phenomena of immunoincompatibility, or even in anaphylactic shock, thus eliminating the possibility of medium/long-term repeated treatments. These adverse effects are eliminated by the enteral or transmucosal way of administration.

Oral or transmucosal absorption of the immunoglobulins complexes according to the present invention presents the following advantages: it allows the protected heterologous immunoglobulins to enter the bloodstream slower to achieve a final systemic effect more gradually. These conditions optimize the interaction between the heterologous Ig and the antigen or the target molecule in the bloodstream. Also the conditions of interaction between the immunocomplex (target molecule or antigen and Immunoglobulin) and the immune system for the clearance of immuno complex are optimized and this reduces immunoreactivity towards the heterologous immunoglobulin. A further advantage is represented by the possibility to rationalize during time the treatment by keeping the levels of the circulating product constant, thus globally enabling a better systemic distribution of immunoglobulins.

The incorporation of Ig into polysaccharides is carried out by using preparations of polysaccharides having different chemico-physical characteristics and with a different degree of derivatization. Polysaccharides are preferably chosen among chitosans with different substituents and their derivatives and polymers and derivatives of alginic acid. Chitosans comprises chitosane with low molecular weight (150,000), chitosane with medium molecular weight (400,000) and with a high degree of deacetylation, glycolchitosane, methylglycolchitosane, Protasan™. Particularly preferred polysaccharides are methylglycolchitosane, chitosane with low molecular weight and high degree of deacetylation and polymannuronic acid (MW 5–10 kD), or the alginate derivatives obtained for instance by enzymatic hydrolysis of alginic acid with alginate-lyase enzyme, and their derivatives or salts. Such polysaccharides or their derivatives are chosen among those which can form around the structure to be incorporated (in the specific case immunoglobulins) a polymeric "film" resistant to enzymatic activity and to chemico-physical variations in the digestive tract, and also enable the possibility to direct the incorporated substance towards mucosal cells, thus enhancing their absorption.

The absence of cross-linking between polysaccharide and Ig is a further advantage of the complexes according to the invention, since the method used for their preparation is easier and the final product does not contain any potentially toxic residues of the chemical cross-linking.

A characteristic of the complexes according to the invention is that polysaccharides coat immunoglobulins without being linked to the latter by means of covalent bonds, but rather forming a sort of surface envelope i.e. in a gel form as in the case of alginic acid.

The immunoglobulins which are incorporated into the polysaccharides are IgG or IgA, or their fragments $F(ab')_2$ or F(ab). They are preferably IgG or their fragments $F(ab')_2$ or F(ab) or biologically active fragments derived for instance by cloning the vanable heavy and light chains of the aforesaid Ig, such as scFv. IgG are prepared by methods known at the state of the art, for instance by immunization of mammals, such as mice, rabbits, etc. as polyclonal immunoglobulins (Johnstone A. & Thorpe, in "Immunochemistry in Practice", 1982, 27–31, Blackwell Sci. Publ. Oxford) or using the technique described for instance in Kohler G. & Milstein C., *Nature* 256:495–497, as monoclonal antibodies. Complexes containing antibodies produced in rabbits, sheep or horses are particularly preferred. Methods for the preparation of the fragments F(ab) or $F(ab')_2$ are known in the art and are for instance described in WO 97/49732. Moreover, immunoglobulins can be also of commercial origin.

The antibodies which are used for the preparation of the complexes according to the invention have different specificities, chosen depending on the desired therapeutic effect. It is understood however that beyond the particular applications mentioned in the present description any complex of immunoglobulins and polysaccharides, in particular chitosane and alginate, their derivatives or substituents, for oral and/or transmucosal use allowing a systemic effect, falls within the frame of the present invention. Immunoglobulins with different specificities can also be combined in one complex so as to obtain a unique or synergic therapeutic effect. According to a particular application in the field of infectious diseases, the complexes according to the invention allow to keep and to improve the use of immunoglobulins in all cases requiring passive immunization, i.e. either in cases when the infective antigen is already present in the organism and an immediate immunoprotection till the development of endogenous antibodies as a consequence of active vaccination is required, or in cases of immunoprophylaxis to prevent infections.

A further and innovative application of the complexes according to the invention is represented by their use in the regulation of physiological biofunctional balances of a given subject by acting on endogenous molecules comprised in the group of: hormones, peptides, obtaining as a result metabolic variations which correct the functional or pathological state of the organism. A further embodiment of the present invention is represented by the possibility to correct functional and metabolic imbalances caused by organic degenerations of various nature and by the possibility to antagonize the accumulation medicine and drug of abuse having as a result the neutralization of toxic effects resulting thereof.

In the field of infectious diseases, said complexes comprises immunoglobulins with a specificity for the following viral agents: Herpes simplex, cytomegalovirus (CMV), chickenpox virus, rubella virus, syncytial virus, respiratory virus, influenza(flue) virus, Epstein-Barr virus, or for their antigenic components, or for the following bacterial agents: *Listeria monocytogenes, Salmonella thipy, S. paratiphy, S. thiphymurium, S. choleraensis, Clostridium tetani, C. botulinum* or *Shigella* etc., or for mycetes, such as *Candida albicans*, or for parasites such as *Toxoplasma gondii*; all other cases where passive immunization is required because of an existing or possible infection are however comprised in the aim of the present invention. Complexes containing anti-*Listeria monocytogenes* and anti-*Salmonella enteriditis* IgG are particularly preferred.

According to this embodiment, the complexes optionally comprise an immunomodulator preferably BVV, represented by the delipidated fraction of *Corynebacterium granulosum*. Alternatively polysaccharidic complexes containing the delipideted fraction of *Corynebacterium* are prepared on their own and administered in combination with the complexes comprising the immunoglobulin. The complexes consisting of polysaccharides and of the delipidated fraction of *Corynebacterium granulosum* are produced in the same way as complexes containing immunoglobulins. The delipidated fraction of *Corynebacterium granulosum* is prepared by growing bacteria in conditions of strict anaerobiosis in mediums and temperature, agitation and time conditions known at the state of the art, such as Bactonutrient broth dehydrated and yeast extract (Difco), in presence of NaCl and glucose. Bacteria are grown for about 30 hours, deactivated by a treatment at high temperature, for instance 30' at 60° C., and then concentrated e.g. by centrifugation. The bacterial mass then undergoes delipidation by a series of extractions in organic solvents, such as for instance 1 extraction in acetone of about 24 hours, followed by an extraction in chloroform (24 hours) and then an extraction in a mixture of methanol-ether in a ratio 1:2 (vol:vol). The sediment of delipidated bacteria then undergoes mechanical breaking by means of a waring Blendor homogenizer, and is then centrifuged at low speed. The supernatant liquor, made of broken bacteria, is further centrifuged at high speed (e.g. 10,000 rpm, for 15–30'). The sediment obtained from this last passage is the BVV particle fraction.

According to a further embodiment immunoglobulins specific for toxins of mycotic origin such as ochratoxin and aflatoxin are used when food intoxication has to be prevented, allowing the clearance of such substances from the bloodstream. Particularly in the zootechnical field it can be necessary to detoxify animals from medicines used for increasing growth (progestinic agents, estrogens, thyrostatic agents, corticosteroids, sympathomimetic agents) or to prevent and/or cure infectious diseases (antibiotics such as oxytetracycline, ampicillin or fungistatics or coccidiostatics such as monensin), so as to ensure the decontamination of the final product (meat, milk, eggs).

According a further embodiment the complexes of the present invention are used to detoxify the organism from: drug of abuse (such as cocaine, LSD, heroine), medicines or hormones.

According to the different embodiments of the invention, the complexes according to the invention for the prevention or the therapy of intoxications, infections or any pathologic states due to exogenous substances or agents, are particularly preferred when the immunoglobulins therein are specific for: ochratoxin, aflatoxin and progesterone, *Listeria monocytogenes* and *Salmonella entheriditis*, for medicines such as monensin and for drugs of abuse, in particular for cocaine.

In case of use of the complexes according to the present invention for passive immunization i.e. for the clearance of the infectious agent or in the prevention of infection, the effect can be strengthened by simultaneous administration of immunomodulators incorporated into the same polysaccharide structures as those used for immunoglobulins together with immunoglobulin or separately. Such immunomodulators are derived from the insoluble fraction consisting of glycoprotein and peptidoglycane or *Corynebacterium granulosum* and are characterized by a significant specific and adjuvating immunostimulating activity. The simultaneous administration of complexes containing a class of immunoglobulins directed towards a given microbic antigen during or after the administration of a non-specific immunomodulator allows to activate the cells involved in the non-specific defense of the organism, also having a synergic effect in the complexing process (formation of circulating immunocomplexes) and in the phagocytosis process of the antigen in combination with specific immunoglobulins.

The complexes according to the invention, which can be absorbed by oral or transmucosal way, are used not only when it is necessary to reduce the hematic level of an external agent (as for the treatment of infectious diseases, or for detoxification from drugs, medicines, toxins, etc.), but also when it is necessary to regulate the endogenous levels of hormones, enzymes and proenzymes, bioactive peptides, precursors and/or metabolites of various nature produced by the organism itself, or any endogenous substances involved in cell biochemistry or in the biochemistry of the whole organism. Said regulation is necessary either to correct pathologic situations due to an alteration in the endogenous balance of said substances, in particular chronic, possibly chronic or degenerative diseases, or to change the biochemical balance of normofunctional subjects, for instance: growth in animals, physical efforts for athletes, pregnancy induction or block, increase of attention threshold, elimination of metabolites deriving from degenerative processes, etc.

In these cases the slow and gradual absorption of immunoglobulins by oral or transmucosal way due to the protective effect of polysaccharides carrying the immunoglobulin, as disclosed in the present invention, allows to carry out therapeutic interventions without parenteral administration.

The complexes according to the present invention are used according to the latter embodiment re-balance the levels of endogenous hormones or enzymes or proenzymes or bioactive peptides involved in the regulation of organic functions. For instance, if it is necessary to vary the levels of endogenous calcium, the complexes according to the invention will contain antibodies or their fragments having a specificity for calcitonin or parathormone, both involved in calcium homeostasis. If it is necessary to intervene in problems related to fat accumulation, for instance in obesity pathogenesis, immunoglobulins will be chosen among those having a specificity for lipases. In other cases related to an imbalance in amino sugar metabolism, Ig will be chosen for example among those having a specificity for β-D-N-acetylglucosaminidase enzyme.

For the regulation of the levels of endogenous substances are particularly preferred complexes containing immunoglobulins or their fragments having a specificity for: somatostatin, glucagon, cholecystoquinine, growth hormone (GH) for growth-related problems; calcitonin and parathormone for problems related to calcium homeostasis. Other preferred complexes are those containing antibodies or their fragments specific for prothrombin (PTT) as anti-thrombosis agents, or for chorionic gonadotropin (ChCG) as anti-pregnancy medicines, or for pentagastrin as anti-ulcer medicines.

Another object of the present invention is the use of the complexes of immunoglobulins and polysaccharides for the preparation of detoxifying medicines with oral and/or transmucosal absorption, with anti-ulcer effects, for the treatment of thromboses and of obesity and their use for the preparation of medicines for the treatment of overdoses in drug addictions, preferably addictions caused by cocaine, heroine or lysergic acid (LSD).

The complexes according to the present invention also consist of immunoglobulins with different specificity, so as to obtain multifunctional complexes, or such to contain also the immunoadjuvant, such as BVV as previously described.

The use of the complexes according to the invention is particularly useful in the zootechnical field for the preparation of food additives to detoxify animals used for the production of meat or milk.

A further object of the present invention consists in compositions for oral use containing as active agent the complexes of immunoglobulins and polysaccharides in combination with suitable adjuvants and excipients, such as for instance those used at the state of the art for the preparation of food granulates for humans and animals (maize starch etc.).

A further object of the present invention consists in compositions for transmucosal use, for instance by perlingual, enteric, nasal, vaginal or rectal way, containing as active agent the complexes according to the invention, which also consist of immunoglobulins having only one or more specificities, in combination with suitable excipients, diluents or solvents; a further object of the invention consists in compositions where adjuvants consist of the immunomodulator BVV, which is present both on its own within the complex and in combination with the immunoglobulins.

The preferred regimen according to the various embodiments, is comprised between 1–100 mg/kg of weight, preferably 5–20 mg/kg, once a day for 7 to 15 days.

For detoxification purposes the regimen may be varied and lowered to 1 to 5 days depending on the degree of intoxication and on the general conditions of the subject.

For the correction of dismetabolism or for the treatment of chronic diseases the treatment may follow the following scheme: once a day for 4 to 7 days with a 2–5 days interruption, then repetition of the treatment.

For the intervention in non-pathological conditions the regimen is preferably comprise between 0,1–100 mg/kg preferably 5–20 mg/kg, once a day for 3 to 10 days, preferably 4 days.

A further embodiment of the present invention is the process for the preparation of the complexes of immunoglobulins and polysaccharides, in particular alginic acid, polymannuronic acid, methylglycolchitosane, chitosane with low molecular weight and high degree of deacetylation, comprising the mixing of a concentrated solution of immunoglobulins (5–50 mg/ml) in $Na_2SO_4$, brought to a temperature between 50 and 60° C. with a solution containing the polysaccharides in a concentration between 0.1 and 10% by weight/volume and mixing by mechanical agitation at maximum speed.

EXPERIMENTAL PART

Example 1

Preparation of the Antibodies (Immunoglobulins)
Preparation of the Immunogens
The immunogens were prepared by conjugation with KLH, or with BSA or ovalbumin, or by fixation with glutaraldehyde. Bacterial immunogens (*Listeria monocytogenes* and *Salmonella entheriditis*) were prepared by inactivation of the microorganism, for instance with formalin and acetone.

The following antigens were conjugated with KLH: Cholesterol-KLH, Pentagastrin-KLH, cholecystoquinine-KHL, calcitonin-KLH (salmon calcitonin), glucagon, monensin. The immunogen of ChG (chorionic gonadotropin) is conjugated with BSA obtaining: BSA-ChG (Chain β), as well as the antigen bovine parathormone (fragment 1–34). The immunogens of prothrombin and of somatostatin were prepared by treatment with glutaraldehyde.

The preparation of the immunogen or vaccine of *Listeria monocytogenes* was carried out by addition of formalin to the microorganism growth suspension till a final concentration of 0.5%. The microorganism culture was carried out for 36 hours at 37° C. in Difco nutrient broth, and by following incubation for 12 hours at room temperature. The bacteria killed in formalin were washed 3 times and resuspended in PBS at a concentration of 1% (v/v). The preparation of the immunogen (vaccine of *Salmonella entheritidis*) was carried out by extraction with acetone for 12 hours at room temperature and by successive (three) washings with sterile physiological solution.

Immunization and Production of the Antibodies

The immunogens described in the previous paragraphs were used in the preparation of the antibodies prepared in rabbits adopting the typical immunization pattern illustrated in Johnstone A. & Thorpe, in "Immunochemistry in Practice", 1982, 27–31, Blackwell Sci. Publ. Oxford.

The treatment pattern for the production of said antibodies was the same for all immunogens. The antibodies were purified by precipitation in a 50% saturated solution of ammonium sulfate according to methods known at the state of the art, such as those described in WO 97/49732. Also antibody fragments F(ab')$_2$ and F(ab) were prepared as described in WO 97/49732, according to methods known at the state of the art.

Example 2

Incorporation of Immunoglobulins into Polysaccharides (Chitosane and Alginate)

Incorporation into Chitosane

For the incorporation of the immunoglobulins chitosane preparations with different characteristics were used, for example: chitosane with low molecular weight (150,000), chitosane with medium molecular weight (400,000) and with a high degree of deacetylation, glycolchitosane, methylglycolchitosane, Protasan™.

Chitosane (MW 750 kD, Fluka 22742) was dissolved at 0.2%–1% in acetate buffer 0.025 M, pH 5.7. The solution of purified IgG (21 g/l) is dissolved in $Na_2SO_4$ 0.05 M (10 mg in 2.5 ml). Each solution was heated in a double boiler to 55° C. 2.5 ml of chitosane solution were added pro 2.5 ml of IgG solution and the mixture was agitated on a vortex at maximum speed for 20–60 seconds.

Incorporation into Alginate

The preparation of IgG in PBS (10 mg in 50 ml) was added with the same volume low viscosity of sodium alginate (Fluka-71238) at 1 to 5% in PBS. The mixture was agitated on a vortex at maximum speed for 30–120 seconds.

Example 3

Preparation of the Adjuvating Complex BVV-Polysaccharides

Preparation of the BVV Fraction from *Corynebacterium granulosum*

The immunomodulator BVV, which is a particle fraction of *Corynebacterium*, was obtained from a microorganism culture. The culture was deactivated by heating (30 minutes) at 60° C. Said culture was then cooled at room temperature and centrifuged, and the bacteria were recovered. The bacterial mass was washed by resuspension in a physiological solution and centrifuged. The washing step was repeated one more time and the bacteria were delipidated by extraction with organic solvents and broken with waring-blendor. Unbroken bacteria were eliminated by centrifugation at low speed for 10 minutes. The supernatant liquor then underwent centrifugation at high speed (10,000 rpm, 30') to recover bacterial fragments. This sediment, mainly consisting of glycoproteins and peptidoglycanes, is the particle fraction known as BVV.

Preparation of the Complexes of the Adjuvant BVV from *Corynebacterium* in Chitosane.

An insoluble particle suspension from *C. granulosum* (BVV) with a concentration of 200 to 2,000 μg/ml in $Na_2SO_4$ 50 mM, was heated in a double boiler at 55° C., and then added with the same volume of chitosane solution at 0.2–4% in acetate buffer 25 mM, pH 5.7. The mixture was heated at 55° C. and vortexed at maximum speed for 30–120 seconds.

Preparation of the Complexes of the Adjuvant BVV from *Corynebacterium* in Alginate.

A volume of BVV suspension of 200 to 2,000 μg pro ml in PBS was added with a sodium alginate solution with low viscosity at 1 to 5% in PBS. The mixture was vortexed at maximum speed for 30–120 seconds.

Example 4

Test on the Absorption of Specific IgG After Oral Administration of the Complexes IgG-alginate and IgG-chitosane The polysaccharide complexes containing specific IgG, in a 1% acacia suspension, were administered through a stomach tube in a constant volume of 1 ml and at concentrations of 10 to 50 mg/kg of specific immunoglobulin.

The absorption of orally administered IgG was then tested by blood withdrawal and dosage of said specific IgG into the serum by the immunoenzymatic method ELISA.

The tests were carried out on Wistar rats weighing 200 g, divided into 3 groups of 20 animals each, which were thus treated:

1st group—control animals, treated only with the carrier;

2nd group—animals treated with specific IgG incorporated into chitosane;

3rd group—animals treated with specific IgG incorporated into alginate.

The tests were carried out on all specific IgG for the various immunogens mentioned in example 1, using the same test conditions.

The blood withdrawal was carried out by intracardiac puncture 3 and 6 hours after the application of the stomach tube. The serum was obtained by blood centrifugation at 3,000 rpm for 15 minutes.

ELISA Protocol

The antigens, as used for immunization and prepared as described in example 1, were adhered to the wells of a microplate by adsorption of 125 μl of a solution containing 4 μg/ml of immunogen in PBS (phosphate saline buffer 0.1 M pH 7.4) at 37° C. for three hours.

Each well was added with 100 μl of animal serum, diluted in PBS (1:5, 1:20, 1:40, 1:80), which were then incubated for 30' at 37° C. to allow the adhesion of specific IgG to the antigen on the microplate. Non-specific IgG were eliminated by washing with physiological solution. The detection of specific antibodies (administered IgG) was carried out by following addition to the well of 100 μl of a solution of an anti-rabbit-immunoglobulin conjugated with a tracing enzyme (anti-rabbit IgG conjugated with peroxidase; SIGMA A 8275) and leaving in contact for 30 minutes at 37° C. The surplus of unlinked conjugate was eliminated by washing and then the chromogen was added (OPD-sigma 6662), thus reading optical density at 492 nm. Said optical density is directly proportional to the concentration of orally administered specific immunoglobulins.

The O.D. results obtained for the various complexes of specific immunoglobulins administered and present in the serum, generally 3 hours after the administration, are listed in tables 1 to 13.

TABLE 1

Detection of anti-ochratoxin IgG present in the bloodstream after oral administration of the complexes according to the invention, using ELISA method

| Anti-ochratoxin IgG | | Average O.D. values | | | |
|---|---|---|---|---|---|
| | | Serum dilutions | | | |
| Group no. | Treatment | 1:5 | 1:20 | 1:40 | 1:80 |
| 1 | controls | 0.031 | — | — | — |
| 2 | Carrier (controls) | 0.368 | 0.238 | 0.105 | 0.054 |
| 3 | IgG in chitosane | 0.891 | 0.880 | 0.608 | 0.460 |
| 4 | IgG in alginate | 0.955 | 0.670 | 0.410 | 0.360 |

TABLE 2

Detection of anti-aflatoxin IgG present in the bloodstream after oral administration of the complexes according to the invention, using ELISA method

| Anti-aflatoxin IgG | | Average O.D. values | | | |
|---|---|---|---|---|---|
| | | Serum dilutions | | | |
| Group no. | Treatment | 1:5 | 1:20 | 1:40 | 1:80 |
| 1 | controls | 0.045 | | | |
| 2 | Carrier (controls) | 0.304 | 0.250 | 0.235 | 0.240 |
| 3 | IgG in chitosane | 0.940 | 0.718 | 0.530 | 0.375 |
| 4 | IgG in alginate | 0.820 | 0.680 | 0.440 | 0.270 |

TABLE 3

Detection of anti-progesterone IgG present in the bloodstream after oral administration of the complexes according to the invention, using ELISA method

| Anti-progesterone IgG | | Average O.D. values | | | |
|---|---|---|---|---|---|
| | | Serum dilutions | | | |
| Group no. | Treatment | 1:5 | 1:20 | 1:40 | 1:80 |
| 1 | controls | 0.024 | | | |
| 2 | Carrier (controls) | 0.220 | 0.200 | 0.160 | 0.160 |
| 3 | IgG in chitosane | 1.050 | 0.930 | 0.750 | 0.560 |
| 4 | IgG in alginate | 1.000 | 0.820 | 0.700 | 0.520 |

TABLE 4

Detection of anti-Listeria monocytogenes IgG present in the bloodstream after oral administration of the complexes according to the invention, using ELISA method

| Anti-L. monocytogenes IgG | | Average O.D. values | | | |
|---|---|---|---|---|---|
| | | Serum dilutions | | | |
| Group no. | Treatment | 1:5 | 1:20 | 1:40 | 1:80 |
| 1 | controls | 0.030 | | | |
| 2 | Carrier (controls) | 0.270 | 0.230 | 0.200 | 0.190 |
| 3 | IgG in chitosane | 1.090 | 0.930 | 0.870 | 0.650 |
| 4 | IgG in alginate | 1.000 | 0.880 | 0.750 | 0.580 |

TABLE 5

Detection of anti-*Salmonella enteriditis* IgG present in the bloodstream after oral administration of the complexes according to the invention, using ELISA method

| Anti-S. entheriditis IgG | | Average O.D. values | | | |
|---|---|---|---|---|---|
| | | Serum dilutions | | | |
| Group no. | Treatment | 1:5 | 1:20 | 1:40 | 1:80 |
| 1 | controls | 0.025 | | | |
| 2 | Carrier (controls) | 0.290 | 0.290 | 0.220 | 0.200 |
| 3 | IgG in chitosane | 0.850 | 0.740 | 0.620 | 0.480 |
| 4 | IgG in alginate | 0.940 | 0.870 | 0.730 | 0.560 |

TABLE 6

Detection of anti-glucagon IgG present in the bloodstream after oral administration of the complexes according to the invention, using ELISA method

| Anti-glucagon IgG | | Average O.D. values | | | |
|---|---|---|---|---|---|
| | | Serum dilutions | | | |
| Group no. | Treatment | 1:5 | 1:20 | 1:40 | 1:80 |
| 1 | White | 0.035 | | | |
| 2 | Carrier (controls) | 0.310 | 0.280 | 0.250 | 0.230 |
| 3 | IgG in chitosane | 0.770 | 0.680 | 0.540 | 0.430 |
| 4 | IgG in alginate | 0.880 | 0.740 | 0.620 | 0.490 |

TABLE 7

Detection of anti-cholecystoquinine IgG present in the bloodstream after oral administration of the complexes according to the invention, using ELISA method

| Anti-cholecystoquinine IgG | | Average O.D. values | | | |
|---|---|---|---|---|---|
| | | Serum dilutions | | | |
| Group no. | Treatment | 1:5 | 1:20 | 1:40 | 1:80 |
| 1 | White | 0.040 | | | |
| 2 | Carrier (controls) | 0.200 | 0.200 | 0.170 | 0.140 |
| 3 | IgG in chitosane | 1.040 | 0.900 | 0.790 | 0.630 |
| 4 | IgG in alginate | 1.100 | 0.950 | 0.800 | 0.660 |

TABLE 8

Detection of anti-parathormone IgG present in the bloodstream after oral administration of the complexes according to the invention, using ELISA method

| Anti-parathormone IgG | | Average O.D. values | | | |
|---|---|---|---|---|---|
| | | Serum dilutions | | | |
| Group no. | Treatment | 1:5 | 1:20 | 1:40 | 1:80 |
| 1 | White | 0.025 | | | |
| 2 | Carrier (controls) | 0.310 | 0.280 | 0.270 | 0.230 |
| 3 | IgG in chitosane | 1.020 | 0.900 | 0.780 | 0.590 |
| 4 | IgG in alginate | 1.080 | 0.750 | 0.630 | 0.490 |

TABLE 9

Detection of anti-prothrombin IgG present in the bloodstream after oral administration of the complexes according to the invention, using ELISA method

| Anti-prothrombin IgG | | Average O.D. values | | | |
|---|---|---|---|---|---|
| | | Serum dilutions | | | |
| Group no. | Treatment | 1:5 | 1:20 | 1:40 | 1:80 |
| 1 | White | 0.025 | | | |
| 2 | Carrier (controls) | 0.200 | 0.150 | 0.130 | 0.130 |
| 3 | IgG in chitosane | 0.800 | 0.660 | 0.530 | 0.390 |
| 4 | IgG in alginate | 0.740 | 0.640 | 0.500 | 0.370 |

TABLE 10

Detection of anti-ChG (chorionic gonadotropin) IgG present in the bloodstream after oral administration of the complexes according to the invention, using ELISA method

| Anti-ChG IgG | | Average O.D. values | | | |
|---|---|---|---|---|---|
| | | Serum dilutions | | | |
| Group no. | Treatment | 1:5 | 1:20 | 1:40 | 1:80 |
| 1 | White | 0.030 | | | |
| 2 | Carrier (controls) | 0.300 | 0.270 | 0.240 | 0.190 |
| 3 | IgG in chitosane | 0.950 | 0.800 | 0.630 | 0.420 |
| 4 | IgG in alginate | 0.900 | 0.790 | 0.600 | 0.350 |

TABLE 11

Detection of anti-pentagastrin IgG present in the bloodstream after oral administration of the complexes according to the invention, using ELISA method

| Anti-pentagastrin IgG | | Average O.D. values | | | |
|---|---|---|---|---|---|
| | | Serum dilutions | | | |
| Group no. | Treatment | 1:5 | 1:20 | 1:40 | 1:80 |
| 1 | White | 0.020 | | | |
| 2 | Carrier (controls) | 0.280 | 0.250 | 0.200 | 0.160 |
| 3 | IgG in chitosane | 1.180 | 1.090 | 0.970 | 0.830 |
| 4 | IgG in alginate | 1.050 | 0.970 | 0.730 | 0.580 |

TABLE 12

Detection of anti-cocaine IgG present in the bloodstream after oral administration of the complexes according to the invention, using ELISA method

| Anti-cocaine IgG | | Average O.D. values | | | |
|---|---|---|---|---|---|
| | | Serum dilutions | | | |
| Group no. | Treatment | 1:5 | 1:20 | 1:40 | 1:80 |
| 1 | White | 0.26 | | | |
| 2 | Carrier (controls) | 0.300 | 0.270 | 0.240 | 0.200 |
| 3 | IgG in chitosane | 0.820 | 0.700 | 0.630 | 0.500 |
| 4 | IgG in alginate | 0.760 | 0.620 | 0.550 | 0.390 |

TABLE 13

Detection of anti-monensin IgG present in the bloodstream after oral administration of the complexes according to the invention, using ELISA method

| Anti-monensin IgG | | Average O.D. values | | | |
|---|---|---|---|---|---|
| | | Serum dilutions | | | |
| Group no. | Treatment | 1:5 | 1:20 | 1:40 | 1:80 |
| 1 | White | 0.30 | | | |
| 2 | Carrier (controls) | 0.270 | 0.240 | 0.230 | 0.200 |
| 3 | IgG in chitosane | 1.040 | 0.930 | 0.840 | 0.730 |
| 4 | IgG in alginate | 1.000 | 0.925 | 0.845 | 0.700 |

The data shown in tables 1 to 13 point out that the complexes according to the invention are orally absorbed and that immunoglobulins are released in the bloodstream; said immunoglobulins are active, as is shown by their specific capacity to recognize the antigen, evaluated according to ELISA. In particular, complexes containing alginate and those in chitosane are both active.

Example 5

Evaluation of the Biological Activity of the Complexes Ig-polysaccharides

The biological activity of immunoglobulins orally administered as complexes was evaluated on rats in various test conditions depending on the effect performed by specific immunoglobulins: elimination of toxic residues from the organism, variation of normofunctional biochemical balances, antagonism of pathogenetic risk factors.

Test on Detoxification of an Animal Treated with Anti-ochratoxin IgG

In order to test the capacity of oral anti-ochratoxin IgG of eliminating the toxin present in the bloodstream, the present test provides for the intoxication of the animal by parenteral administration of said toxin. Considering the short half-life of the toxin and the times required for the absorption of the orally administered complexes, the detoxifying agent (complexes with anti-ochratoxin IgG) was administered to the animal before intoxication. The dosage of detoxifying IgG was established on the basis of a preliminary intoxication experiment carried out in order to evaluate half-life and hematic levels reached by the toxin in vivo in animals having the same weight. IgG dosage was calculated considering that 1 mole of IgG can link 2 moles of toxin in optimal conditions.

The preliminary experiments were carried out on male rats weighing 200±10 g divided into groups of 20 units each, using the following experimental pattern: a group of animals was administered ochratoxin by subcutaneous way in a dose of 200 µg/kg; after 3, 6, 9 hours blood was drawn by intracardiac puncture and centrifuged at 3,000 rpm for 15 minutes for serum separation. Serum samples were obtained and used for determining hematic levels of ochratoxin using HPLC methods (M. Ospital, J. M. Carabeie, A. M. Betbeder, C. Tricard, E. Creppy and B. Medina, *L'Ochratoxine, A dans les vins*, Revue Francaise d'Enologie, March/April 1998, n. 169).

Once hematic levels and the speed of toxin elimination from blood were established, a group of 20 rats having the same average weight as before was orally treated with anti-ochratoxin IgG incorporated into chitosane with a molar dose 5 times above the number of millimoles of toxin dosed into the blood; incorporated IgG were administered in a 2% acacia suspension. After 1.5 hours ochratoxin, always in a dose of 200 µg/kg, was injected subcutaneously into the animals.

3, 6, 9 hours after said administration blood was drawn and serums separated as before. The ochratoxin content of the gathered serum samples was then analyzed.

The table shows the proportional decrease of the hematic content of ochratoxin in the animals pretreated with IgG incorporated into chitosane with respect to the animals which have received the toxin only.

TABLE 14

% Elimination of ochratoxin in rats pretreated with anti-ochratoxin IgG incorporated into chitosane, and then intoxicated with ochratoxin

| Time after intoxication hours | % elimination of hematic toxin |
|---|---|
| 3 | 60 |
| 6 | 100 |
| 9 | 100 |

The data contained in the table point out that by using the complexes according to the invention the elimination of toxin from the bloodstream is completed after 6 hours only. Test on the Biological Activity of the Complexes Anti-somatostatin IgG Incorporated into Chitosane or Alginate.

The biological activity of the complexes of anti-somatostatin was measured by analyzing the growth curves of the animals treated with said complexes.

The tests were carried out on growing rats weighing 80±5 g divided into groups of 10 animals which received:

| Group 1 | Controls, no treatment; |
|---|---|
| Group 2 | Treated with anti-somatostatin IgG incorporated into chitosane in a dose of 100 µg/kg every 7 days through a stomach tube in a 2% acacia suspension; |
| Group 3 | Treated with anti-somatostatin IgG incorporated into alginate in a dose of 100 µg/kg every 7 days through a stomach tube in a 2% acacia suspension. |

All 3 groups of animals received daily, together with food, 20 mg/kg of L-arginine and 20 mg/kg of DL-aspartic acid as exogenous activators of the growth hormone (GH); the animals drank freely.

The weight of every single animal was checked every 7 days for a period of 1 month.

Table 15 shows the proportional differences between the average values of the weights of the animals orally treated with anti-somatostatin IgG and control animals.

TABLE 15

Proportional differences between the average values of the weights of the animals orally treated with anti-somatostatin IgG and control animals

| Group | Treatment | Weight % on days: | | | | |
|---|---|---|---|---|---|---|
| | | 0 | 7 | 14 | 21 | 28 |
| 1 | Carrier (controls) | — | — | — | — | — |
| 2 | Anti-somatostatin IgG in chitosane | — | +2 | +9.0 | +13.8 | +24.5 |
| 3 | Anti-somatostatin IgG in alginate | — | +4 | +8.5 | +12.7 | +23.6 |

The data contained in the table point out that the complexes containing anti-somatostatin IgG antagonize the endogenous release of somatostatin resulting from the induction of Growth Hormon by administration of L-arginine and DL-aspartic acid. The evident result is a growth increase due to the use of nutritional activators only.

Test on the Biological Activity of the Complexes Anti-prothrombin IgG Incorporated into Chitosane or Alginate.

The effect of the administration of anti-prothrombin IgG incorporated into chitosane or alginate on the coagulating activity was measured on mice by tail coagulation assay.

Swiss mice weighing 20 g, both male and female, were divided into groups of 10 animals and treated as follows:

| Group 1: | Controls, oral administration of 0.5 ml of a 2% acacia solution; |
|---|---|
| Group 2: | Treated, oral administration (stomach tube) of 5 mg/kg of anti-prothrombin IgG incorporated into chitosane and resuspended in 2% acacia; |
| Group 3: | Treated, oral administration (stomach tube) of 5 mg/kg of anti-prothrombin IgG incorporated into alginate and resuspended in 2% acacia. |

After 2 hours the animals of all three groups were treated by subcutaneous injection of 0.3 ml of a 3% calcium chloride solution.

On the third hour the end portion of the animals' tail was cut with a razor blade and then immersed in a bath of physiological solution thermoregulated at 37° C.

Blood dripping times (dripping ended) were checked as index of the endogenous production of thrombin and therefore of the activation of the coagulation cascade. The proportional difference between dripping times in the animals treated with the complexes of anti-prothrombin IgG in polysaccharides, administered through stomach tube, and those in control animals is shown in table 16; these results show that anti-prothrombin IgG administered as described can reduce the bioavailability of thrombin physiological precursor.

TABLE 16

Effect of the complexes of anti-prothrombin IgG

| Group | Treatment | % variation of dripping times of mouse tail |
|---|---|---|
| 1 | Control | — |
| 2 | Orally treated with anti-prothrombin IgG in chitosane | +17.5% |

TABLE 16-continued

Effect of the complexes of anti-prothrombin IgG

| Group | Treatment | % variation of dripping times of mouse tail |
|---|---|---|
| 3 | Orally treated with anti-prothrombin IgG in alginate | +15.0% |

Test on the Biological Activity of the Complexes Anti-ChG (Chorionic Gonadotropin) IgG Incorporated into Chitosane or Alginate.

The analysis of the effects of administration of anti-ChG IgG in chitosane or alginate was carried out by evaluating pregnancy induction in rats.

The tests were carried out on female Wistar rats weighing 200 g±10, divided into groups of 50 animals and treated as follows:

| Group 1: | Controls, no treatment; |
|---|---|
| Group 2: | Treated with anti-ChG IgG incorporated into chitosane; |
| Group 3: | Treated with anti-ChG IgG incorporated into alginate. |

Every 4 days for the whole inbreeding period the animals receive a dose of the complexes according to the invention, corresponding to 10 mg/kg of IgG through a stomach tube in a 2% acacia suspension.

Female rats were kept in cages containing 5 animals each, can freely eat and drink, and a sexually mature male rat is introduced into every cage (male Wistar rat weighing 250 g); said male rat is kept in the cage for 20 days from the beginning of the test.

After said period the male rat was removed from the cage and the female rats were transferred into single cages; the treatment with anti-ChG IgG is suspended. The number of pregnancies (deliveries) was then checked on the female rats.

Table 17 shows the proportional decrease of the number of pregnancies in the animals treated with the complexes containing anti-ChG IgG through a stomach tube, with respect to control animals.

TABLE 17

% decrease of pregnancies

| Group | Treatment | % decrease of pregnancies |
|---|---|---|
| 1 | Controls | — |
| 2 | Treated with anti-ChG IgG in chitosane | 85% |
| 3 | Treated with anti-ChG IgG in alginate | 78% |

The data contained in table 17 show that the treatment with complexes according to the invention containing anti-ChG IgG highly reduces the number of pregnancies in the animals used, both for complexes in alginate and in chitosane.

Test on the Biological Activity of the Complexes of Anti-cocaine IgG Incorporated into Chitosane or Alginate.

The analysis of the effects resulting from the administration of anti-cocaine IgG in chitosane or alginate on cocaine anesthetic response was carried out on mice using the hot plate test according to the description made by O. Bagasra et al. (*Immunopharmacology*, 1992, 23:173).

Swiss mice weighing 20 g, male, divided into groups of 20 animals, are treated as follows:

| | |
|---|---|
| Group 1: | Controls, the animals receive 0.5 ml of 2% acacia through a stomach tube. |
| Group 2: | Treated with anti-cocaine IgG incorporated into chitosane. |
| Group 3: | Treated with anti-cocaine IgG incorporated into alginate. |

The animals received through a stomach tube a dose of complexes according to the invention corresponding to 20 mg/kg of IgG resuspended in 0.5 ml of 2% acacia.

After 3 hours all the animals received by intraperitoneal way 25 mg/kg of cocaine in physiological solution.

After one hour the animals were placed on a plate thermoregulated at 55° C., checking the time of reactivity of the animal to thermal stimulation in seconds.

Table 18 shows proportional variations of the responses with respect to test animals who have received only cocaine.

TABLE 18 shows proportional variations of the responses with respect to test animals who have received only cocaine.

| Group | Treatment | % decrease of response time to thermal stimulation |
|---|---|---|
| 1 | Controls | — |
| 2 | Pre-treated with anti-cocaine IgG in chitosane p.o. | 50.0% |
| 3 | Pre-treated with anti-cocaine IgG in alginate p.o. | 46.0% |

The data in the table show that the complexes according to the invention, orally administered and containing anti-cocaine antibodies, perform their function by removing cocaine from the bloodstream. The effect which has been observed, therefore, is the reduction of the times of reaction to the stimulation with respect to animals treated only with cocaine.

Test on the Biological Activity of the Complexes of Anti-*Salmonella* IgG Incorporated into Chitosane or Alginate, Associated or Not with BVV.

The analysis of the effects resulting from the administration of anti-*Salmonella* IgG in chitosane or alginate, in association or not with BVV, on the prevention of the clinical development of salmonellosis is carried out in mice.

The tests were carried out on groups of 20 Swiss mice weighing 20 g, which are treated as follows:

| | |
|---|---|
| Group 1: | Controls: normally fed animals; |
| Group 2: | Treated with anti-Salmonella IgG incorporated in chitosane on days 0, 7 and 14; |
| Group 3: | Treated in anti-Salmonella IgG incorporated into chitosane, associated with complexes containing the particle fraction BVV incorporated into chitosane at a dose of 2 mg/kg, resuspended in the same 2% acacia suspension. |

The animals received through a stomach tube a dose of complexes according to the invention corresponding to 5 mg/kg of IgG resuspended in 0.5 ml of 2% acacia.

On the 15$^{th}$ day the animals are orally inoculated with a dose of *Salmonella entheriditis* corresponding to $10^9$ microorganisms. The animals were then divided and kept in single cages, checking the possible onset of clinical episodes of salmonellosis.

Table 19 shows the percentages of animals which have developed salmonellosis in the three groups.

TABLE 19 shows the percentages of animals which have developed salmonellosis in the three groups.

| Group | Treatment | % of clinical infections |
|---|---|---|
| 1 | Controls | 85 |
| 2 | Orally pretreated with anti-Salmonella IgG in chitosane | 20 |
| 3 | Orally pretreated with anti-Salmonella IgG in chitosane in association with BVV in chitosane | 0 |

The data contained in table 19 show that passive vaccination with anti-*Salmonella* IgG in chitosane by oral administration is enough to prevent the onset of the experimental infection to a high extent.

Said activity is strengthened by the simultaneous administration of complexes containing a non-specific immunomodulator (BVV) administered in the same form and modalities as anti-*Salmonella* antibodies.

What is claimed is:

1. An isolated composition consisting of immunoglobulins as the active ingredient, a polysaccharide selected from the group consisting of chitosanes and alginates, wherein the polysaccharidic molecules are neither chemically cross-linked to the immunoglobulins, nor to each other, in combination with suitable excipients and diluents.

2. The composition according to claim 1, wherein the immunoglobulins and the polysaccharides are associated by means of non-covalent links.

3. The composition according to claim 1, wherein the chitosanes are selected from the group consisting of chitosanes with a molecular weight below 150,000 Da, methylglycolchitosane, and salts thereof.

4. The composition according to claim 3, wherein the chitosane is metilglicolchitosane or its salts.

5. The composition according to claim 1, wherein the alginates are selected from the group consisting of polymannuronic acid, alginic acid and its enzymatic fragments, and salts thereof.

6. The composition according to claim 1, wherein said immunoglobulins are selected from the group consisting of IgG, IgA, or their fragments F(ab')$_2$ or F(ab) or scFv.

7. The composition according to claim 6, wherein said immunoglobulins are IgG or their fragments F(ab')$_2$ or F(ab) or scFv.

8. The composition according to claim 1, wherein said immunoglobulins are specific for substances selected from the group consisting of toxins, infectious agents, hormones, enzymes, proenzymes, drugs of abuse, medicines, bioactive peptides, metabolites, physiologic precursors and their antigenic components.

9. The composition according to claim 8, wherein said toxins are of mycotic origin.

10. The composition according to claim 9, wherein said toxins are selected from the group consisting of ochratoxin, aflatoxin, zearalonon and fumonisine.

11. The composition according to claim 8, wherein the infectious agents are selected from the group consisting of Herpes simplex virus, cytomegalovirus (CMV), chickenpox virus, rubella virus, syncytial virus, respiratory virus, influenza virus, Epstein-Barr virus, *Listeria monocytogenes, Salmonella thipy, Salmonella entheriditis, Salmonella paratiphy, Salmonella thiphymurium, Salmonella*

*choleraensis, Clostridium tetani, Clostridium botulinum* or *Shigella, Candida albicans,* and *Toxoplasma gondii.*

12. The composition according to claim 8, wherein said drugs of abuse are selected from the group consisting of cocaine, heroin, lysergic acid or their derivatives.

13. The composition according to claim 8, wherein said medicines are selected from the group consisting of monensin, corticosteroids, antibiotics, anticoccidiostatics, antivirus, fungicides, chemiotherapic agents and sympathomimetic agents.

14. The composition according to claim 8, wherein said substances are selected from the following group:

a) somatostatin, glucagon cholecystoquinine and growth hormone;

b) parathormone and calcitonin;

c) pentagastrin;

d) thyroid hormone; and e) prothrombin.

15. The composition according to claim 11, for the preparation of food additives.

16. The composition according to claim 1, for oral and transmucosal administration.

17. The composition according to claim 16, wherein said transmucosal administration is perlingual, rectal, vaginal, or buccal.

\* \* \* \* \*